US007192601B2

(12) United States Patent
Walker

(10) Patent No.: US 7,192,601 B2
(45) Date of Patent: Mar. 20, 2007

(54) ANTIMICROBIAL AND SPORICIDAL COMPOSITION

(76) Inventor: Edward B. Walker, 3655 Mt. Ogden Dr., Ogden, UT (US) 84403

( * ) Notice: Subject to any disclaimer, the term of this patent is extended or adjusted under 35 U.S.C. 154(b) by 423 days.

(21) Appl. No.: 10/346,216

(22) Filed: Jan. 16, 2003

(65) Prior Publication Data

US 2004/0058878 A1 Mar. 25, 2004

Related U.S. Application Data

(60) Provisional application No. 60/350,416, filed on Jan. 18, 2002.

(51) Int. Cl.
*A01N 25/22* (2006.01)

(52) U.S. Cl. ................ 424/405; 424/78.07; 424/78.09; 424/401; 424/613; 424/667; 514/557; 514/568; 514/643; 514/675; 514/724

(58) Field of Classification Search ................ 424/405, 424/613, 667, 78.09, 78.07, 401; 514/724, 514/675, 557, 643, 730, 568
See application file for complete search history.

(56) References Cited

U.S. PATENT DOCUMENTS 3,968,250 A 7/1976 Boucher
4,272,395 A 6/1981 Wright
4,923,899 A 5/1990 Wachman et al.
5,405,602 A 4/1995 Simmons et al.
5,490,980 A * 2/1996 Richardson et al. ....... 424/94.6
5,637,307 A 6/1997 Simmons et al.
5,985,929 A 11/1999 Kern
6,001,864 A * 12/1999 Akashi et al. ............. 514/399
6,020,375 A 2/2000 Nishihata et al.
6,022,551 A 2/2000 Jampani et al.
6,183,807 B1 2/2001 Gutzmann
6,228,385 B1 5/2001 Shick
6,238,682 B1 * 5/2001 Klofta et al. ............... 424/402
6,248,343 B1 * 6/2001 Jampani et al. ............. 424/405

FOREIGN PATENT DOCUMENTS

GB 1539771 * 2/1979
GB 2 300 565 11/1996
JP WO96/12404 5/1996

OTHER PUBLICATIONS

Fabiola P. Chea et al, Modeling the Germination Kinetics of *Clostridium botulinum* 56A Spores as Affected by Temperature, pH, and Sodium Chloride†, Journal of Food Protection, vol. 63, No. 8, 2000, p. 1071-1079.

(Continued)

*Primary Examiner*—Neil S. Levy
(74) *Attorney, Agent, or Firm*—Thorpe North & Western LLP

(57) ABSTRACT

Germicidal compositions with enhanced activity towards killing microbiological spores and vetgetative cells comprising certain quaternary ammonium compounds (QACs), phenolic compounds, monohydric alcohols, hydrogen peroxide, iodine, triclocarban, triclosan or combinations thereof with one or more spore coat opening agents. The invention also provides for the application of the germicidal compositions to animate and inanimate surfaces to help kill germs and protect against the risk of infection from bacteria, molds, yeasts, fungi, viruses, and microbiological spores.

7 Claims, 2 Drawing Sheets

OTHER PUBLICATIONS

Patrice Dion† et al, Germination Properties as Marker Events Characterizing Later Stages of *Bacillus substilis* Spore Formation, Journal of Bacteriology, Feb. 1980, p. 786-792.

Abdelmadjid Atrih et al, The Role of Peptidoglycan Structure and Structural Dynamics During Endospore Dormancy and Germination, Antonie van Leeuwenhoek 75: 299-307, 1999.

K. P. McCann et al, Alanine Germination Receptors of *Bacillus subtilis*, Letters in Applied Microbiology 1996, 23, 290-294.

S. J. Foster et al, Pulling the Trigger: the Mechanism of Bacterial Spore Germination, Molecular Microbiology (1990) 4(1), 137-141.

Padmavathy Venkatasubramanian et al, Biochemical Analysis of the *Bacillus subtilis* 1604 Spore Germination Response, Journal of General Microbiology (1989), 135, 2723-2733. Printed in Great Britain.

A-K, J. Sallal et al, Effect of Date Extract on Growth and Spore Germination of *Bacillus subtilis*, Microbios 59 p. 203-210 1989.

Yoko Yasuda et al, Relation Between D-Glucose and L- and D-Alanine in the Initiation of Germination of *Bacillus subtilis* Spore, Microbiol.Immunol. vol. 28 (2), 197-207, 1984.

Yoko Yasuda et al, Germination-Initiation and Inhibitory Activities of L- and D-Alanine Analogues for *Bacillus subtilis* Spores, Microbiol. Immunol. vol. 29 (3), 229-241,1985.

Yoko Yasuda-Yasaki et al, Inhibition of *Bacillus subtilis* Spore Germination by Various Hydrophobic Compounds: Demonstration of Hydrophobic Character of the L-Alanine Receptor Site, Journal of Bacteriology, Nov. 1978, p. 484-490.

Yoko Yasuda et al, Quantitative Structure-Inhibitory Activity Relationships of Phenols and Fatty Acids for *Bacillus subtilis* Spore Germination, J. Med. Chem. 1982, 25, 315-320.

Yuzaburo Ishida et al, Temperature-pH Effect Upon Germination of Bacterial Spores, Can. J. Microbiol. vol. 22, 1976.

Pieter P.M. Bonsen et al, Biochemical Studies of Bacterial Sporulation and Germination, Journal of Bacteriology, Apr. 1969, p. 62-68.

Richard Wax et al, Initiation of the Germination of *Bacillus subtilis* Spores by a Combination of Compounds in Place of L-Alanine, Journal of Bacteriology, Feb. 1968, p. 433-438.

S. P. Gorman et al, Death, Injury and Revival of Chemically Treated *Bacillus subtilis* Spores, Journal of Applied Bacteriology, 1983, 54, 91-99.

A. S. Kamat et al, Mechanism of $Ca^{2+}$and Dipicolinic Acid Requirement for L-alanine Induced Germination of *Bacillus cereus* BIS-59 Spores, Microbios 44 33-44 1985.

* cited by examiner

Alkyltrimethyl ammonium chloride

Dialkyldimethylammonium chloride

Alkyldimethylbenzylammonium chloride

Alkyldimethyl(ethylbenzyl)ammonium chloride

Benzethonium chloride

ANTIMICROBIAL AND SPORICIDAL COMPOSITION

This application claims the benefit of U.S. Provisional Application No. 60/350,416 filed on Jan. 18, 2002.

BACKGROUND OF THE INVENTION

1. Field of the Invention

The present invention relates generally to germicidal disinfecting compositions. More particularly, the present invention relates to a novel concept for germicidal disinfecting compositions that are effective in killing both vegetative microorganisms and microbiological spores in a single composition.

2. Related Art

Microbiological spores are among the most resilient forms of dormant life known to man. Although formed by many different types of microbiological organisms, the most commonly studied spores are from various *Bacillus* or *Clostridium* species. In particular, Bacillus spores are amazingly resistant to common sterilizing techniques. For example, most vegetative bacteria die quickly when subjected to temperatures in excess of 80° C., but bacterial spores often survive boiling water at 100° C. for two hours or more. Spores have survived for 20 years in 70% alcohol solutions and can survive one million rems of radiation. Drying has little effect on spores, as demonstrated by spores surviving in the intestines of Egyptian mummies for thousands of years. [I. Edward Alcamo, (2001) *Fundamentals of Microbiology, 6th* ed., Jones and Bartlett Publishers, Sudbury, Mass.].

Spores are formed by bacteria when nutritional resources are low. The resulting spores have certain compartments and layers. The central core, referred to as the protoplast, contains soluble enzymes and genetic material. The spore protoplast is surrounded by a spore membrane that functions as a boundary for the spore protoplast, as a regulator of cell permeability, and as a structural matrix for certain enzymes. A germ cell wall is immediately external to the spore membrane, composed primarily of peptidoglycan. The next layer is the spore cortex, also composed of modified peptidoglycan. Many of the properties of the protective cortex layer are attributed to this component such as the regulation of spore size and permeability. The spore coat represents 30–60% of the dry spore weight, contains approximately 80% of the total spore proteins, and occupies about 50% of the spore volume. The spore coat is extremely resistant to a variety of drastic chemical treatments, suggesting that the coat plays an important role in spore resistance. The exposporium, or outermost spore layer varies in structure and composition from species to species of bacteria.

Spores remain dormant until germination is triggered by external stimuli. Many types of spores are activated by heat or by certain chemical substances such as calcium dipicolinate and amino acids, most particularly L-alanine. Activation is the initial event in germination, an irreversible process that converts dormant spores into metabolically active ones within a short period of time. Initiation of germination is followed rapidly by a number of degradative changes in the spore. The protective coating around the spore begins to open and becomes more permeable to water, causing the germinated spores to swell. Reducing agents that reduce disulfide cystine linkages in proteins and enzymes that attack peptidoglycan linkages also weaken the spore coat and increase permeability of the spore. As germination proceeds, the spores shed their outer layers, allowing the young, vegetative cells to emerge, elongate, and divide. Development of a vegetative cell from a germinated spore is called outgrowth.

A safe and effective topical skin care formulation capable of killing microbiological spores and preventing their subsequent development into infectious, vegetative cells is desired and needed. Furthermore, it is also desired that the formulation be gentle to skin, provide a cosmetically pleasing feel and assist in gently moisturizing the skin, such that the user will gain benefit from both the microbiocidal activity and improved skin health through repetitive application.

SUMMARY OF THE INVENTION

It has been recognized that it would be advantageous to develop germicidal composition with enhanced microbiocidal activities for killing microbiological spores, microbiological outgrowth from spores, and vegetative microorganisms. The invention provides a germicidal composition with enhanced microbiocidal activities for killing microbiological spores, microbiological outgrowth from spores, and vegetative microorganisms and a method of use thereof.

In a first embodiment, the composition of the present invention comprises at least one quaternary ammonium compound selected from the group consisting of a quaternary ammonium compound containing a $C_{18-30}$ alkyl substituent, benzethonium chloride, benzethonium bromide, benzethonium iodide, methylbenzethonium chloride, methylbenzethonium bromide, and methylbenzethonium iodide. Preferably, the quaternary ammonium compound is present in a concentration of about 0.01% to 10%, and a more preferably in a concentration of about 0.05% to 8%, or an optimal concentration of about 0.08% to 5%.

In a second embodiment, the composition comprises an antibacterial agent and a spore coat opener.

In this embodiment, the antibacterial agent is a member selected from the group consisting of a quaternary ammonium compound, a phenolic compound, a monohydric alcohol, hydrogen peroxide, iodine, triclocarban, triclosan or combinations of such antibacterial agents.

The concentration of the antibacterial agent may vary depending upon the class selected. The quaternary compound may be present in a concentration of about 0.01% to 10%, or more preferably in a concentration of about 0.05% to 8%, or in an optimal concentration of about 0.08% to 5%. The phenolic compound is selected from the group consisting of phenol, para-chlorometaxylenol, cresol, and resorcinol, and hexylresorcinol and may be present in a concentration of about 0.01% to 10%, or more preferably in a concentration of about 0.01% to 5%, or in an optimal concentration of about 0.05% to 1%. The monohydric alcohol is selected from the group consisting of ethyl alcohol and isopropyl alcohol, and may be present in a concentration of about 20% to 95%, or more preferably in a concentration of about 20% to 70%, or in an optimal concentration of about 25% to 70%. The hydrogen peroxide may be present in a concentration of about 1% to 10%, or more preferably in a concentration of about 1% to 5%, or in an optimal concentration of about 2% to 4%. The iodine may be present in a concentration of about 0.1% to 10%, or more preferably in a concentration of about 0.5% to 8%, or in an optimal concentration of about 1% to 5%. The triclocarban or triclosan may be present in a concentration of about 0.01% to 5.0%, or more preferably in a concentration of about 0.05% to 3%, or in an optimal concentration of about 0.05% to 2%.

As noted, in the second embodiment, the composition of the present invention also contains at least one spore coat opener selected from the group consisting of an amino acid, a metal chelation agent, a reducing agent or an emulsifier, or a surface-active agent or a mixture of any or all of these agents.

Preferably, the amino acid is selected from the group consisting of alanine, glycine, valine, leucine, isoleucine, proline, serine, threonine, methionine, cysteine, taurine, tyrosine, phenylalaine, tryptophan, asparagine, glutamine, aspartic acid, glutamic acid, lysine, arginine, and histidine, and combinations thereof including their free acid forms and their salts. The amino acid is present in a concentration of about 0.0001% to 5%, or more preferably in a concentration of about 0.001% to 2%, or in an optimal concentration of about 0.005% to 1%.

The metal chelation agent is selected from the group consisting of EDTA, EGTA, picolinic acid, nicotinic acid, niacin, citric acid, ascorbic acid, glutamic acid, and fulvic acid, and combinations thereof including their free acid forms and their salts. The chelation agent is present in a concentration of about 0.001% to 5%, or more preferably in a concentration of about 0.01% to 2%, or in an optimal concentration of about 0.05% to 1%.

The reducing agent is selected from the group of substances or combinations of substances that are capable of reducing disulfide bonds, including ascorbic acid, quinone, polyphenol with up to hundreds of polymeric subunits including but are not limited to: phenol-rich polymers of flavonoids, gallic acid, ellagic acids and their respective carbohydrate esters, salts and derivatives, and proanthocyanidin, including their free acid forms. The reducing agent is present in a concentration of about 0.001% to 2%, or more preferably in a concentration of about 0.001% to 1%, or in an optimal concentration of about 0.005% to 0.5%.

The emulsifier/surface-active agent is selected from the group consisting of $C_{12-24}$ monohydric alcohols, $C_{2-18}$ monohydric alcohol ethoxylates, $C_{8-24}$ alkylamine oxides, silicone copolyols, the quaternary ammonium compounds behentrimethylammonium, babassuamindopropalkonium, benzethonium, benzalkonium, a $C_{8-24}$ mono-alkylquaternary ammonium, a $C_{8-24}$ di-alkylquaternary ammonium and the like, combined with their respective anionic salt counterparts chosen from the group of halogens such as chloride, bromide, or iodide, methosulfate, ethosulfate, acetate, lactate, propionate, and the like. The emulsifier/surface-active agent is present in a concentration of about 0.1% to 25%, or more preferably in a concentration of about 0.5% to 15%, or in an optimal concentration of about 1% to 10%. Combinations of two or more emulsifier/surface-active agents may also be utilized.

Additional features and advantages of the present invention will be apparent from the detailed description which follows, taken in conjunction with the accompanying drawings, which together illustrate, by way of example, features of the invention.

DETAILED DESCRIPTION

Before the present composition and methods of making and using thereof are disclosed and described, it is to be understood that this invention is not limited to the particular configurations, as process steps and materials may vary somewhat. It is also intended to be understood that the terminology employed herein is used for the purpose of describing particular embodiments only and is not intended to be limiting since the scope of the present invention will be limited only by the appended claims and equivalents thereof. It must be noted that, as used in this specification and the appended claims, the singular forms "a," "an," and "the" include plural referents unless the context clearly dictates otherwise.

"germ" refers to a small mass of living substance capable of developing into an organism or one of its parts; a microorganism causing disease.

"germicide" refers to an agent that destroys or deactivates germs.

Reference will now be made to the exemplary embodiments illustrated and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

This invention relates to germicidal compositions with enhanced germicidal activities for killing microbiological spores, vegetative cells that arise from spores, bacteria, viruses, molds, yeasts, fungi, and the like. Expanded activity of germicidal compositions is provided by the inclusion of agents such as amino acids, metal chelation agents, reducing agents, or surface-active agents that open or weaken spore coats thereby increasing permeability to the germicidal agents. Therefore, the novel combination of spore coat opening agents with antimicrobial agents expands their traditional activities to include significantly enhanced and expanded activity against spores.

The invention also provides for the application of the germicidal compositions to animate and inanimate surfaces to help prevent the risk of infection from bacteria, molds, yeasts, viruses, fungi, and microbiological spores.

Figure 1:
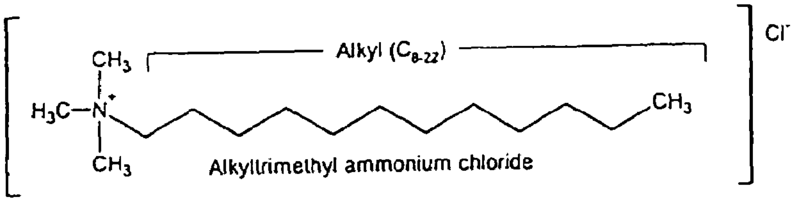
FIG. 1 illustrates generalized chemical structures of quaternary ammonium chloride compounds with antimicrobial activity.
Figure 1:
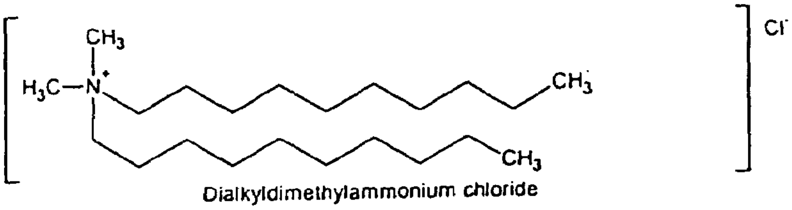
Figure 1:
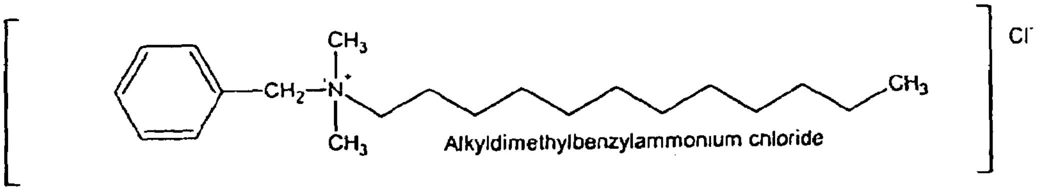
Figure 1:
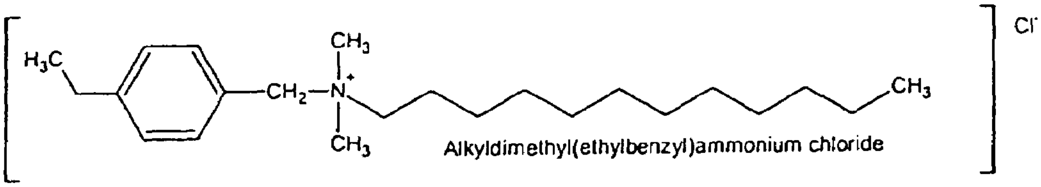
Figure 1:
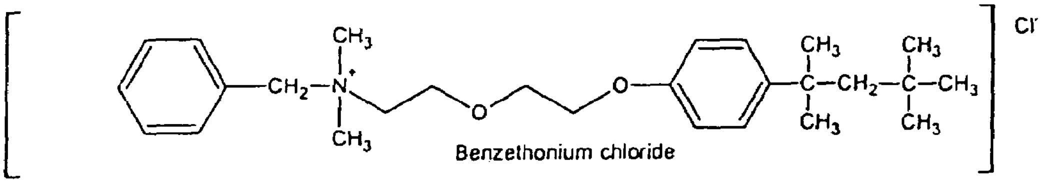

The invention describes germicidal compositions that contain one or more antimicrobial and sporicidal active ingredients. In particular, quaternary ammonium compounds (QACs) are well known for their antibacterial action against certain types of vegetative cells. An important aspect of this invention is the application of specific classes of QACs as sporicidal agents per se. Certain surface-active QACs exhibit sporicidal activity, such as linear alkyl and benzylalkonium chlorides, dialkyldimethylammonium chlorides, and the rather unique QAC: benzethonium chloride (BEC). The chemical structure of BEC represents a creative departure from the relatively simple alkyl groups substituted on the quaternary nitrogen. The distinguishing feature of this rather complex molecule is best described by BEC's IUPAC name, N,N-Dimethyl-N-[2-[2-[4-(1,1,3,3-tetramethylbutyl) phenoxy]ethoxy]ethyl]benzene-methanaminium chloride. As seen in FIG. 1, this complex nitrogen substituent contains branched hydrocarbons, phenoxy, and ethoxy components. Ethoxylation increases detergency and the complex nature of this group enhances the spectrum of activity when compared to more traditional QACs. The unique chemical character of BEC establishes it as a very different class of QACs. BEC's sporicidal activity, or its method of use in destroying microbiological spores has not previously been reported.

An important aspect of the present invention is to combine ingredients into a formulation that will help to open up the protective spore coatings, so as to facilitate the entry of antimicrobial ingredients into the inner core of the spores where they can interrupt normal spore functions, thus killing or inactivating the spore more effectively than without such additives. Furthermore, the new formulation may be in the form of a oil-in-water emulsion that is very stable in both freezing and elevated storage temperatures which enhances product stability.

Another aspect of the invention is to insure that the formulation offers a variety of ingredient combinations to assist those skilled in the art in developing combinations of these ingredients into desirable germicidal products.

As noted above, certain QACs are both antimicrobial and sporicidal. Other QACs are antimicrobial only.

Low molecular weight alcohols are excellent antimicrobial active ingredients. However, due to the very different anatomy and function of spores as compared to vegetative forms of infectious organisms, alcohols are not sporicidal. In fact, aqueous-alcoholic solutions are the storage medium of choice for bacterial spores. Spores survive intact for years when stored in aqueous-ethanol solutions.

Conversely, aldehydes, phenols, parabens, elemental halogens, and ozone can inhibit various steps of the spore germination process following activation during subsequent outgrowth. To this point in time, only low molecular weight aldehydes have been shown to demonstrate sporicidal activity against dormant spores, prior to their activation. It is known that combining one or more of these sporicidal agents often results in a more active composition. For example combinations of QACs with dialdehydes has been a particularly active combination in cold sterilizers for inanimate surfaces.

One particularly important aspect of the present invention relates to the combination of active sporicides with other ingredients that are not independently sporicidal resulting in a composition that works synergistically with enhanced sporicidal activity. Combining sporicidal agents with substances that exhibit spore-activating properties for the purpose of enhancing sporicidal activity provides a novel aspect of the invention. Three such useful groups of spore-activating ingredients are amino acids, divalent metal chelates, and mild reducing agents. Unlike the sporicidal agents, these latter ingredients stimulate the dormant spore, through various mechanisms, to initiate a breakdown of the protective coating around the spore, causing a weakening of the spore coating. The resulting gaps and channels and increased permeability in the spore coating allow penetration of biocidal agents into the spore core and inner membranes, where they can act to destroy the spore more effectively.

The invention also makes use of a similar effect on spore coat weakening that can be achieved by incorporating an emulsion of oil and water to weaken and open the spore coat, making the spore more susceptible to damage. The premature opening of the spore coat caused by contact with such an emulsion can quickly lead to loss of internal components and subsequent dysfunction. In particular, the use of a positively-charged emulsifying agent in the emulsion adds significantly to the activity of the emulsion, since it is attracted to the proteinaceous spore coat, where the positively charged oil-water interface denatures the proteins and breaks down the spore's protective coating. If desired, sporicidal agents can also be included in the composition to increase the effectiveness of the emulsion by taking advantage of the emulsion-damaged spore coat to penetrate into the spore and destroy the metabolically important components inside.

Still another aspect of the invention relates to added benefits to skin, including moisturizing and skin-softening properties associated with emulsions. Emollients, colors, and fragrances may be added to enhance the cosmetic appeal of the product. Since emulsions include both water and oil phases, a wide variety of such additives are possible without negatively affecting the sporicidal activity. When applied to the skin as a leave-on product, emulsions can help extend protection for hours beyond the initial application. When an emulsion is formulated with increased levels of non-volatile components, the sporicidal protection of the composition may be extended for longer periods of time.

The key to spore resistance is the integrity of the spore coat and the low water content of the spore protoplast. Upon activation and subsequent germination, the spores become much more susceptible to sporicidal and bactericidal agents. Bactericidal agents such as alcohols, most quaternary ammonium compounds, phenols, hydrogen peroxide, iodine, triclocarban and triclosan exhibit very poor sporicidal activity per se. However, combining these agents with one or more spore coat opening agents dramatically expands their efficacy against spores. Increased permeability of the spore coat allows these agents to more readily penetrate the protective coating, allowing them access to vital sites within the spore. Therefore, the novel combination of spore coat opening agents with these antimicrobial agents expands their traditional activities beyond vegetative cells to include significantly enhanced and expanded activity against spores. Applications for such combinations include enhanced antimicrobial lotions, handwashes, creams, gels, soaps, cleansers, first-aid antiseptics, rinse and no-rinse sanitizers, and the like applied to both animate and inanimate surfaces.

The present invention provides for safe and effective topical skin care formulations capable of killing microbiological spores, preventing their subsequent development into infectious, vegetative cells, and destroying vegetative cells that result from outgrowth of spores. Furthermore, the novel formulation is gentle to skin, providing a cosmetically pleasing feel and assisting in gently moisturizing the skin, such that the user will gain benefit from both the sporicidal activity and improved skin health through repetitive application. Certain embodiments of the invention are also useful for cleaning and sterilizing hard surfaces.

Therefore, in one embodiment the present invention provides a germicidal composition with enhanced microbiocidal activities for killing microbiological spores, microbiological outgrowth from spores and vegetative microorganisms comprising at least one quaternary ammonium compound selected from the group consisting of a quaternary ammonium compound containing a $C_{18-30}$ alkyl substituent, benzethonium chloride, benzethonium bromide, benzethonium iodide, methylbenzethonium chloride, methylbenzethonium bromide, and methylbenzethonium iodide. The quaternary ammonium compound is present in a concentration of about 0.01% to 10%, or more preferably in a concentration of about 0.05% to 8%, or in an optimal concentration of about 0.08% to 5%. The composition can be applied to healthy, infected, or wounded tissue such as epithelial tissues, skin, fingernails, toenails, hair, mammary glands, the perineal region, genitalia, rectum, and mucosal linings of the nose and/or the vaginal area in the form of a liquid spray, dipping solution, foam, lotion, cream, handwash, wet wipe, or the like, to prevent and/or protect against the risk of infection. When applied to skin or an inanimate surface, the composition cleans the surface effectively, removing dirt, soil, oils, and the like.

In another embodiment, the present invention also provides a germicidal composition with enhanced microbiocidal activities for killing microbiological spores, microbiological outgrowth from spores, and vegetative microorganisms, containing at least one active microbiocidal agent and at least one spore coat opener. The combination of the microbiocidal agent and spore coat opener is sporicidal. A preferred microbiocidal agent, which is also a sporicidal agent per se includes a quaternary ammonium halide compound selected from the group of benzethonium, methylbenzethonium, benzalkonium, a $C_{8-24}$ mono-alkyl quaternary ammonium, a $C_{8-24}$ di-alkylquaternary ammonium chloride or bromide, or the like. Other quaternary ammonium quaternary ammonium compounds, which are microbiocidal but not effectively sporicidal also combine with spore coat openers to become sporicidal. Exemplary of such quaternary ammonium compounds are simple quaternary ammonium compounds like cetrimonium and benzalkonium halides.

The quaternary ammonium compound is present in a concentration of about 0.05% to 10%, or more preferably in a concentration of about 0.08% to 8%, or in an optimal concentration of about 0.08% to 5%.

Another example of a microbiocide that, in the presence of a spore coat opener, becomes a sporicidal agent is a phenolic compound chosen from the group consisting of phenol, para-chlorometaxylenol, cresol, resorcinol, hexylresorcinol, or the like. The phenolic compound is present in a concentration of about 0.01% to 10%, or more preferably in a concentration of about 0.01% to 5%, or in an optimal concentration of about 0.05% to 1%.

In addition, when combined with a spore coat opener, hydrogen peroxide can be used as a sporicidal agent when present in a concentration of about 1% to 10%, or a more preferable concentration of about 1% to 5%, or an optimal concentration of about 2% to 4%.

Another microbiocide that, in the presence of a spore coat opener, becomes sporicidal includes iodine, in a concentration of about 0.1% to 10%, or more preferably in a concentration of about 0.5% to 8%, or in an optimal concentration of about 1% to 5%.

Furthermore, a compound selected from the group of triclocarban, triclosan, and the like, in a concentration of about 0.01% to 5%, or more preferably in a concentration of about 0.05% to 3%, or in an optimal concentration of about 0.05% to 2% becomes sporicidal in the presence of a spore coat opener.

Suitable spore coat openers includes amino acids such as alanine, glycine, valine, leucine, isoleucine, proline, serine, threonine, methionine, cysteine, taurine, tyrosine, phenylalaine, tryptophan, asparagine, glutamine, aspartic acid, glutamic acid, lysine, arginine, histidine, or the like, including their free acid forms and their salts, wherein the amino acid or combinations of amino acids are present in a concentration of about 0.0001% to 5%, or more preferably in a concentration of about 0.001% to 2%, or in an optimal concentration of about 0.005% to 1%.

Another class of spore coat openers includes metal chelation agents chosen from the group consisting of EDTA, EGTA, picolinic acid, nicotinic acid, niacin, citric acid, ascorbic acid, glutamic acid, fulvic acid, and the like, including their free acid forms and their salts. The chelation agent is present in a concentration of about 0.001% to 5%, or more preferably in a concentration of about 0.01% to 2%, or in an optimal concentration of about 0.05% to 1%.

Further a reducing agent that is capable of reducing disulfide bonds such as ascorbic acid, quinone, polyphenol, proanthocyanidin, or the like, including their free acid forms and their salts can also be used as spore coat openers. The reducing agent is present in a concentration of about 0.001% to 2%, or more preferably in a concentration of about 0.001% to 1%, or in an optimal concentration of about 0.005% to 0.5%.

The composition of the present invention optionally contains at least one hydrophobic component chosen from the group consisting of petrolatum, mineral oil, dimethicone, synthetic or naturally occurring oils, and the like, wherein the hydrophobic component is present in a concentration of about 0.1% to 70%, or more preferably in a concentration of about 1% to 50%, or in an optimal concentration of about 1% to 35%.

The composition may also contain at least one emollient/solubilizer, chosen from the group consisting of selected from the group consisting of $C_{12-24}$ monohydric alcohols, $C_{2-18}$ monohydrohyric alcohol ethoxylates, $C_{8-24}$ alkylamine oxides, silicone copolyols, the quaternary ammonium compounds behentrimethylammonium, babassuamindopropalkonium, benzethonium, benzalkonium, a $C_{8-24}$ mono-alkylquaternary ammonium, a linear $C_{8-24}$ di-alkylquatemary ammonium and the like, combined with their respective anionic salt counterparts chosen from the group of halogens such as chloride, bromide, or iodide, methosulfate, ethosulfate, acetate, lactate, propionate, and the like. The emollient/solubilizer is present in a concentration of about 0.1% to 25%, or more preferably in a concentration of about 0.5% to 15%, or in an optimal concentration of about 1% to 10%.

Suitable emulsifiers for the present invention include positively-charged, amphoteric, neutral or non-ionic surface-active agents. The amphoteric or zwiterionic emulsifiers have both positive and negative charges on the same emulsifier. A good example is a "betaine", such as cocoamidopropyl betaine or behenyl betaine (amphoteric surfactants) or a "sultaine", such as cocamidopropyl hydroxysultaine or erucamidopropyl hydroxysultaine. All of the positively-charged antimicrobial quaternary ammonium compounds described in this application also may serve a dual role in their respective formulations as emulsifiers. In addition to these, other positively-charged surface-active agents may be utilized as emulsifiers, such as hydroxyethyl behenamidopropyl dimonium chloride. Example nonionic emulsifiers includes the following: sorbitan esters and ethoxylates such as: sorbitan stearate, sorbitan oleate, sorbitan isostearate, polysorbate 20, polysorbate 60, polysorbate 80, PEG-20 sorbitan isostearate; ethoxylated modified glycerides such as: PEG-20 (almond or corn) glycerides, PEG-60 (almond or corn) glycerides, PEG-45 palm kernel glycerides, PEG-6 caprylic/capric glycerides, PEG-7 glyceryl cocoate; Alkyl ethoxylates such as: Ceteth-20, PEG-30 caster oil, oleth-3, oleth-5, oleth-10, oleth-20, glycereth-31, steareth-2, steareth-10, and stereth-20; Carbohydrate esters such as: sucrose distearate, sucrose distearate, sucrose cocoate, and the like; propoxylates such as: PPG-12 butyl ether, PPG-10 butanediol, PPG-10 cetyl ether, PPG-3 myristyl ether; alkanolamides such as: cocamide DEA, lauramide DEA, stearamide DEA, and the like; amino oxides such as: behenamine oxide, cocamidopropylamine oxide, lauramine oxide, myristamine oxide, stearamine oxide; lanolin and lanolin derivatives and silicone copolyols.

The present invention also provides a method for disinfecting surfaces and killing microbiological spores, microbiological outgrowth from spores, vegetative microorganisms, viruses, molds, yeasts, and fungi comprising the step of applying a liquid to a surface, said liquid containing a composition of the present invention.

Since many modifications, variations and changes in detail can be made to the described preferred embodiment of the invention, it is intended that all matters in the foregoing description and the following examples are interpreted to illustrate, and not in any way to limit, the invention.

EXAMPLE GROUP A

This type of sporicidal formulation contains one or more surface-active quaternary ammonium compounds, water, a polyhydric alcohol, one or more preservatives, and if desired, additives to enhance the cosmetic aspects of the formula such as fragrance, color, viscosity builders, emollients, and the like.

Group A Examples: Sporicidal Liquid Formulations

| | A1 | A2 | A3 | A4 | A5 |
|---|---|---|---|---|---|
| Distilled Water | 98.16% | 97.30% | 97.68% | 97.10% | 96.58% |
| Benzethonium chloride, USP | 0.20% | | | | 0.20% |
| Stearalkonium chloride | | | | 0.20% | |
| Behentrimonium chloride | | | | 0.05% | |
| Behentrimonium methosulfate | | | | | 0.10% |
| Benzalkonium chloride, 80% | | | 0.16% | | |
| Cetrimonium chloride, 30% | | | 0.50% | | 0.50% |
| para-chlorometaxylenol | | 0.20% | | 0.10% | |
| Glycerin | 1.40% | | 1.00% | | 2.00% |
| Propylene glycol | | 2.00% | | 2.00% | |
| Methylparaben | 0.02% | 0.02% | 0.03% | 0.02% | 0.02% |
| Propylparaben | 0.02% | 0.02% | 0.03% | 0.02% | 0.02% |
| Cocoamidopropylbetaine, 30% | 0.05% | | 0.10% | | 0.02% |
| Ceteth-20 | | 0.05% | | 0.05% | 0.05% |
| Squalane | 0.01% | | | | 0.10% |
| Aloe vera extract | | 0.01% | | 0.01% | 0.01% |
| Vitamin E Acetate | | | 0.10% | 0.05% | |
| Fragrance & Preservatives | q.s. | q.s. | q.s. | q.s. | q.s. |

EXAMPLE GROUP B

These sporicidal formulations are similar to the Examples in Group A, but to which is added one or more water-insoluble hydrophobes appropriate for application to the skin with appropriate emollients and/or solubilizers.

Example Group B: Sporicidal Compositions with Hydrophobes and Emollient/Solubilizers

| | B1 | B2 | B3 | B4 | B5 |
|---|---|---|---|---|---|
| Water Phase: | | | | | |
| Water | 68.0% | 78.1% | 82.7% | 85.0% | 73.7% |
| Glycerin | 2.5% | 2.5% | 2.5% | | |
| Propylene glycol | | 2.5% | | 2.50% | 2.5% |
| Benzethonium chloride | | 0.2% | 0.2% | 0.5% | |
| Cetrimethylammonium chloride-30% | | | 0.5% | 0.1% | |

-continued

Example Group B: Sporicidal Compositions with Hydrophobes and Emollient/Solubilizers

| | B1 | B2 | B3 | B4 | B5 |
|---|---|---|---|---|---|
| para-chlorometaxylenol | | | | 0.1% | 0.1% |
| Aloe Vera Extract | 0.1% | | 0.1% | | 0.1% |
| Cucumber Extract | | 0.1% | 0.1% | | |
| Oil Phase: | | | | | |
| Mineral Oil | 11.4% | 5.2% | 4.4% | | 6.5% |
| Petrolatum | 6.6% | | | 3.0% | 2.6% |
| Isopropyl Myristate | | 8.3% | 3.2% | | 3.9% |
| Isocetyl Stearate | | | 0.3% | 4.3% | 0.5% |
| Dimethicone-350 | | 0.8% | 2.0% | | 1.0% |
| Stearalkonium chloride | 4.0% | | | | 2.8% |
| Ceteryl alcohol | 6.5% | 5.0% | 3.9% | 4.1% | 5.2% |
| Behentrimonium chloride | | 2.1% | | | |
| Behentrimonium methosulfate | | | 1.4% | | 2.3% |
| Babassuamidopropalkonium chloride | | | | 2.0% | |
| Vitamin E Acetate | 0.1% | 0.1% | 0.1% | 0.1% | 0.1% |
| Preservatives and Fragrance: | q.s. | q.s. | q.s. | q.s. | q.s. |

Mixing Directions:

Mix ingredients for Water Phase and heat to 80° C. with mixing.

Mix ingredients for Oil Phase and heat to 80° C. with mixing in a separate vessel.

Combine Oil Phase and Water Phase with homogenization and/or agitation.

Cool to below 50° C.; add preservatives and fragrance.

EXAMPLES GROUP C

These examples demonstrate novel compositions containing various sporicidal agents in combination with spore coat opening agents.

Group C Examples: Sporicidal Liquid Formulations with Spore Coat Opening Agents

| | C1 | C2 | C3 | C4 | C5 |
|---|---|---|---|---|---|
| Distilled Water | 98.06% | 96.90% | 97.34% | 35.19% | 96.00% |
| Benzethonium chloride, USP | 0.20% | | 0.20% | | 0.20% |
| Stearalkonium chloride | | | 0.12% | | |
| Behentrimonium chloride | | | | | 0.10% |
| Behentrimonium methosulfate | | | 0.10% | | |
| Benzalkonium chloride, 80% | | 0.20% | | | 0.20% |
| Cetyltrimethylammonium chloride, 30% | | | 0.50% | | 0.50% |
| para-chlorometaxylenol | | 0.20% | | | |
| Ethyl alcohol, 95% | | | | 61.00% | |
| Glycerin | 1.40% | | 1.40% | | 2.50% |
| Propylene glycol | | 2.00% | | 2.00% | |
| Methylparaben | 0.02% | 0.02% | 0.02% | | 0.02% |
| Propylparaben | 0.02% | 0.02% | 0.02% | | 0.02% |
| Cocoamidopropylbetaine, 30% | 0.05% | | 0.05% | | |
| Ceteth-20 | | 0.05% | | | 0.05% |
| Isopropyl myristate | | | | 1.20% | |
| Squalane | 0.01% | | 0.01% | | 0.01% |
| Aloe vera extract | | 0.01% | | 0.01% | |
| Vitamin E Acetate | | | | 0.10% | 0.10% |
| Fragrance | 0.09% | 0.20% | 0.09% | 0.20% | |
| Kathon | 0.05% | | 0.05% | | 0.05% |

-continued

| Group C Examples: Sporicidal Liquid Formulations with Spore Coat Opening Agents | | | | | |
|---|---|---|---|---|---|
| | C1 | C2 | C3 | C4 | C5 |
| Sodium hydroxymethyl-glycinate | | 0.20% | | 0.20% | |
| Amino acid Mixture | | 0.20% | | 0.01% | 0.20% |
| L-alanine | 0.10% | | | | |
| Calcium dipicolinate | | | 0.10% | | 0.05% |
| Disodium EDTA | | 0.1% | | 0.01% | |
| Quinone | | | | 0.05% | |
| Proanthocyanidin | | | 0.05% | | |

EXAMPLES

GROUPS D AND E

Formulations such as taught in Examples A, B, and C are enhanced with respect to sporicidal activity by combining one or more ingredients that are known to trigger spore germination with hydrophobic components and appropriate emollients and solubilizers. These examples are representative of the possible combinations of these components.

| Examples D&E: Sporicidal Emulsions Enhanced with Spore Coat Opening Agents | | | | | |
|---|---|---|---|---|---|
| | D1 | E1 | E2 | E3 | E4 |
| Water Phase: | | | | | |
| Water | 67.8% | 77.8% | 82.6% | 84.9% | 73.6% |
| Glycerin | 2.5% | 2.5% | 2.5% | | |
| Propylene glycol | | 2.5% | | 2.5% | 2.5% |
| Benzethonium chloride | | 0.2% | 0.2% | 0.5% | |
| Cetrimethylammonium chloride-30% | | | 0.5% | 0.1% | |
| para-chlorometaxylenol | | | | 0.1% | 0.1% |
| Aloe Vera Extract | 0.1% | | 0.1% | | 0.1% |
| Cucumber Extract | | 0.1% | 0.1% | | |
| Amino acid Mixture | | 0.3% | | | |
| L-alanine | | | 0.1% | | |
| Calcium dipicolinate | 0.2% | | | | |
| Disodium EDTA | | | | 0.1% | |
| Reducing Agent | | | | | 0.1% |
| Oil Phase: | | | | | |
| Mineral Oil | 11.4% | 5.2% | 4.4% | | 6.5% |
| Petrolatum | 6.6% | | | 3.0% | 2.6% |
| Isopropyl Myristate | | 8.3% | 3.2% | | 3.9% |
| Isocetyl Stearate | | | 0.3% | 4.3% | 0.5% |
| Dimethicone-350 | | 0.8% | 2.0% | | 1.0% |
| Stearalkonium chloride | 4.0% | | | | 2.8% |
| Ceteryl alcohol | 6.5% | 5.0% | 3.9% | 4.1% | 5.2% |
| Behentrimonium chloride | | 2.1% | | | |
| Behentrimonium metho-sulfate | | | 1.4% | | 2.3% |
| Babassuamidopropal-konium chloride | | | | 2.0% | |
| Vitamin E Acetate | 0.1% | 0.1% | 0.1% | 0.1% | 0.1% |
| Preservatives and Fragance: | q.s. | q.s. | q.s. | q.s. | q.s. |
| Mixing Directions: | | | | | |

Mix ingredients for Water Phase and heat to 80° C. with mixing.
Mix ingredients for Oil Phase and heat to 80° C. with mixing in separate vessels.
Combine oil and water phases with homogenization and/or agitation.
Cool to below 50° C., add preservatives and fragrance.

Test Methods and Results:

Spore suspensions were prepared by streaking standard agar plates with *Bacillus subtilis* and then incubating the plates for 48–72 hours at 37° C. The resulting bacteria and their spores were scraped from the plates and suspended by agitation in a 50% ethanol-water solution for four hours in order to lyse the vegetative cells. The spores were collected by centrifugation, washed three times and then suspended in 50% ethanol-water, resulting in a spore titer of $10^9$ spores/mL. Aliquots of this spore suspension were diluted 1:100 into representative embodiments of the invention in order to demonstrate sporicidal activity. After treatment, the spore suspensions were diluted in distilled water and duplicate aliquots from each dilution were pour-plated on tripticase soy agar. Total colony-forming units (cfu) were counted after incubation at 37° C. for 24 hours. Sporicidal activity was directly proportional to the reduction of cfu compared to the distilled water controls.

Figure 2:
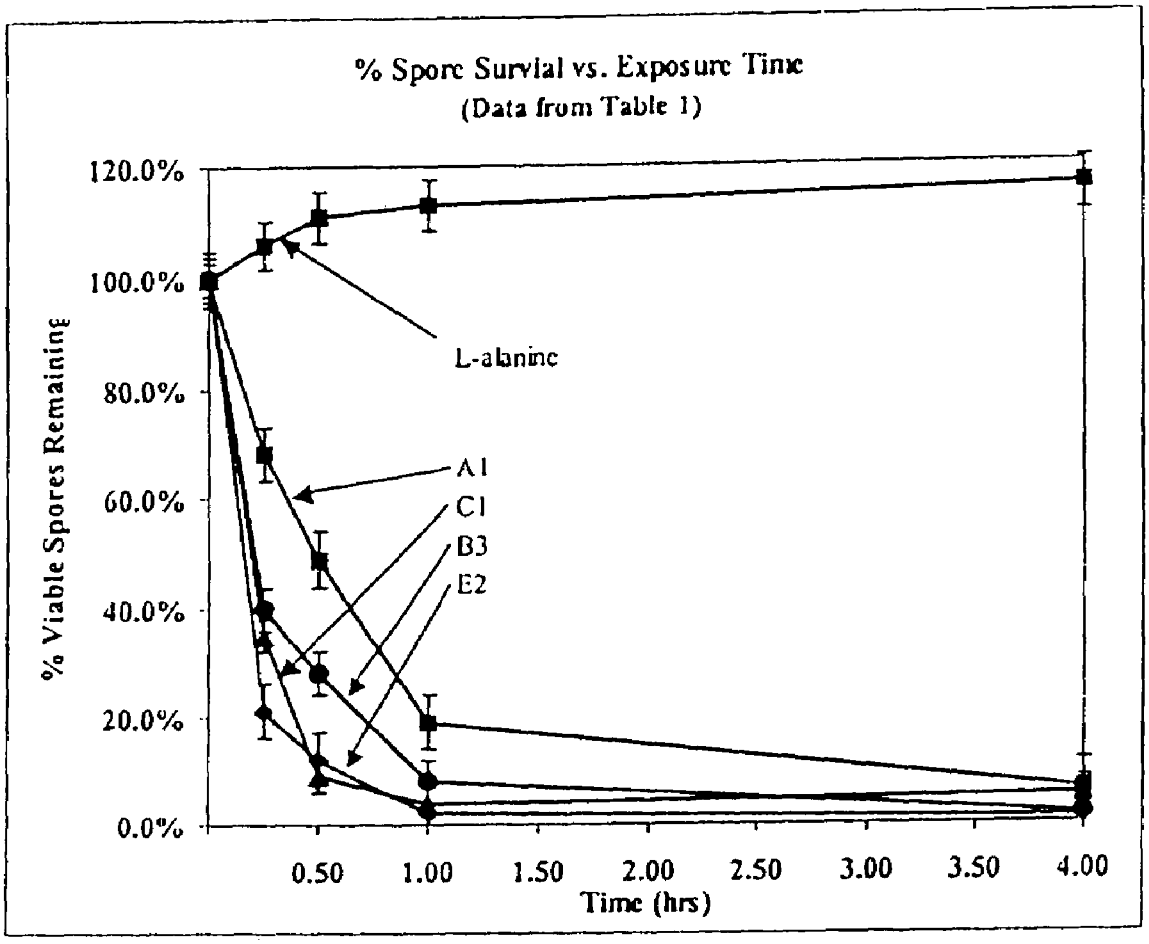
FIG. 2 is graphic illustration of the test results of spore-inactivating compositions of the present invention.

Test results from representative compositions are summarized in Table 1 and the associated graph of the data (FIG. 2). In addition, test data for exposure to 0.1% L-alanine in the absence of sporicidal agents is included. This demonstrates enhancement of the germination process by L-alanine as it helps to open the spore coat more effectively.

TABLE 1

| Test results of Spore-inactivating Compositions vs. Exposure Time | | | | | |
|---|---|---|---|---|---|
| Time(hrs) | L-alanine | A1 | C1 | B3 | E2 |
| 0.00 | 100.0% | 100.0% | 100.0% | 100.0% | 100.0% |
| 0.25 | 106.0% | 68.0% | 35.0% | 40.0% | 21.0% |
| 0.50 | 111.0% | 49.0% | 9.0% | 28.0% | 12.0% |
| 1.00 | 113.0% | 19.0% | 4.0% | 8.0% | 2.2% |
| 4.00 | 116.0% | 6.4% | 5.2% | 1.6% | 0.1% |

Similar experiments were also carried out against another type of spore. *Clostridium sporogenes* (ATCC# 7955) was chosen as a representative of the *Clostridium* genus for this test. Spores were exposed to 15-second and 30-second exposures to formulation B3. When suspensions of these spores were exposed to formula B3 ($10^7$/mL final) for 15 seconds, reduction of 85% was observed. Exposure for 30 seconds under the same conditions resulted in a reduction of 99.9%.

It is to be understood that the above-described arrangements are only illustrative of application of the principles of the present invention. Numerous modifications and alternative arrangements can be devised without departing from the spirit and scope of the present invention. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variation in size, materials, shape, form, function and manner of operation, assembly and use may be made without departing from the principles and concepts set forth herein.

What is claimed is:

1. A germicidal composition with enhanced microbiocidal activities for killing or disinfectng microbiological spores, microbiological outgrowth from spores and vegetative microorganisms comprising water (75–85%), glycerin (1–5%), benzethonium chloride (0.1–0.2%), 30% cetrimethylammonium chloride (0.1–3%), alanine (0.05–3%), mineral oil (2–7%), isopropyl myristate (1–6%), isocetyl stearate (0.1–5%), dimethicone (0.5–3.0%), ceteryl alcohol (2–6%) and behentrimonium methosulfate (0.3–5%).

2. A method for disrupting and subsequently destroying microbiological spores and microbiological outgrowth from spores on surfaces comprising the step of applying the composition of claim 1 to said surface.

3. The method of claim 2, wherein the surface is a member selected from the group consisting of epithelial tissues, skin, fingernails, toenails, hair, mammary glands, perineal region, genitalia, rectum and mucosal linings.

4. The method of claim 2, wherein the surface is an inanimate surface.

5. The method of claim 2, wherein the composition is applied to a surface in the form of a spray, dipping solution, foam, lotion, cream, handwash, or wet wipe.

6. An antimicrobal skin cream, lotion or handwash composition with enhanced microbiocidal activities for killing or disinfecting microbiological spores, microbiological outgrowth from spores and vegetative microorganisms comprising alanine (0.05–3%), behentrimonium methosulfate (0.5–4%), benzethonium chloride (0.05–0.5%), ceteryl alcohol (1–8%), 30% cetrimethylammonium chloride (0.1–8%), dimethicone (0.5–5%), glycerin (0.5–4%), isocetyl stearate (0.1–1.0%), isopropyl myristate (0.5–5%), mineral oil (1–7%), propylene glycol (0.5–3%) and water (75–85%).

7. The composition of claim 6 formulated as a first aid antiseptic.

* * * * *